United States Patent
Mafune et al.

(10) Patent No.: US 6,412,936 B1
(45) Date of Patent: Jul. 2, 2002

(54) INK, INK SET, INK CARTRIDGE, RECORDING UNIT, IMAGE RECORDING PROCESS AND IMAGE RECORDING APPARATUS

(75) Inventors: Kumiko Mafune, Kawasaki; Yutaka Kurabayashi, Murayama; Koromo Shirota; Masashi Ogasawara, both of Kawasaki, all of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/257,510

(22) Filed: Feb. 25, 1999

(30) Foreign Application Priority Data

Mar. 3, 1998 (JP) ............................. 10-050510

(51) Int. Cl.$^7$ ............................................. G01D 11/00
(52) U.S. Cl. ......................... 347/100; 347/101; 347/96
(58) Field of Search ................. 347/100, 101, 347/106, 95, 96; 106/31–58

(56) References Cited

U.S. PATENT DOCUMENTS

| | | | |
|---|---|---|---|
| 5,213,613 A | 5/1993 | Nagashima et al. | 106/20 R |
| 5,540,764 A * | 7/1996 | Haruta et al. | 347/100 |
| 5,549,740 A | 8/1996 | Takahashi et al. | 106/20 R |
| 5,571,313 A | 11/1996 | Mafune et al. | 106/22 H |
| 5,734,403 A * | 3/1998 | Suga et al. | 347/101 |
| 5,764,261 A | 6/1998 | Koike et al. | 347/100 |
| 5,782,967 A * | 7/1998 | Shirota et al. | 106/31.58 |
| 5,928,388 A * | 7/1999 | Leaver | 8/638 |
| 5,952,414 A * | 9/1999 | Noguchi et al. | 524/377 |
| 5,997,124 A * | 12/1999 | Capps et al. | 347/14 |
| 5,997,623 A * | 12/1999 | Lin | 106/31.58 |
| 6,015,455 A * | 1/2000 | Yano et al. | 106/31.58 |

FOREIGN PATENT DOCUMENTS

| | | | |
|---|---|---|---|
| EP | 0 602 914 A1 | 6/1994 | |
| EP | 0 769 536 A2 | 4/1997 | |
| JP | 54-59936 | 5/1979 | |
| JP | 6-271798 | 9/1994 | |
| JP | 10-768 | 1/1998 | |
| JP | 10095107 | * 4/1998 | ............... B41J/2/01 |

* cited by examiner

*Primary Examiner*—John Barlow
*Assistant Examiner*—Manish S. Shah
(74) *Attorney, Agent, or Firm*—Fitzpatrick, Cella, Harper & Scinto

(57) ABSTRACT

The invention provides an ink including a water-soluble coloring material and bis(hydroxyethyl)sulfone in an aqueous medium and having a pH of from 9.5 to 12. The ink permits stable formation of high-quality images on a wide variety of recording media, and has excellent ejection stability, ejection durability and storage stability.

31 Claims, 4 Drawing Sheets

MOVING DIRECTION OF CARRIAGE

INK, INK SET, INK CARTRIDGE, RECORDING UNIT, IMAGE RECORDING PROCESS AND IMAGE RECORDING APPARATUS

BACKGROUND OF THE INVENTION

1. Field of the Invention

The present invention relates to an ink suitable for use in, particularly, ink-jet recording in which an ink is ejected from an orifice in response to recording signals to conduct recording on a recording medium, and an ink set, ink cartridge, recording unit, image recording apparatus and image recording process using

2. Related Background Art

Inks with various compositions have heretofore been reported and proposed for inks to be used for ink-jet recording. In particular, in recent years, detailed research and developments have been made from various approaches such as composition and physical properties of inks so that a good record can be made even on plain paper such as paper for copying, paper for reporting, notepaper and letter paper, which are commonly used in offices, or even on cloth.

Various systems have also been proposed for ink-jet recording methods, including a system wherein charged ink droplets are continuously ejected to use a part thereof for recording, a system wherein signals are given to a recording head having a piezoelectric element, and an ink is ejected in response to the signals to conduct recording, a system wherein thermal energy according to recording signals is applied to an ink within a recording head by means of, for example, a heater, and the ink is ejected by the thermal energy to conduct recording, etc. Such an ink-jet recording method using a system wherein an ink is ejected by the bubbling phenomenon of the ink caused by thermal energy as described in, for example, Japanese Patent Application Laid-Open No. 54-59936 is a main system for ink-jet recording methods at present from the view point that high integration and high density assembly of openings from which an ink is ejected (hereinafter referred to as "orifices") are conducted with ease. By the way, examples of preferred characteristics or properties that inks used in ink-jet recording should have include the following characteristics or properties:

(1) providing clear or bright images having a high optical density;

(2) providing high-quality images free of any undefined or irregular feathering;

(3) having high fixing ability to recording media;

(4) being excellent in ejection stability; and (5) having good storage stability.

With the demands for further speeding up of printing, multi-coloring of images, still higher definition of images and still higher image quality in recent years, recording media of various types have also been developed according to their application fields, and there is thus the demand for development of inks which meet the above-described characteristics (1) to (3) at a higher level irrespective of recording media and moreover satisfy the above-described characteristics (4) and (5) at a high level.

In response to such a demand, for example, Japanese Patent Application Laid-Open No. 6-271798 discloses an ink comprising bis(hydroxyethyl)sulfone (hereinafter abbreviated as "BHES") as an ink satisfying the provision of high-quality images, good fixing ability to recording media and good ejection stability scarcely causing clogging at an orifice.

SUMMARY OF THE INVENTION

As the results of investigations carried out by the present inventors up to this time, the following findings have been obtained.

Namely, when a water-based ink containing no BHES is used in the system wherein the ink is ejected by means of a heater, kogation derived from a water-soluble coloring material in the ink gradually occurs on the heater, and this kogation prevents stable ejection of the ink and moreover adversely affects the formation of high-quality images.

In addition, the addition of BHES to the water-based ink can effectively prevent the occurrence of kogation derived from the water-soluble coloring material on the heater.

Under such circumstances, the present inventors have carried out further investigation as to inks containing a water-soluble coloring material and BHES in an aqueous medium with a view toward further improving the above-described characteristics. As a result, it has been found that when the pH of such an ink is adjusted to 9.5 to 12, particularly, 9.5 to 11, the effect of preventing the occurrence of kogation on the heater is more enhanced, and such adjustment is also effective for improvement in the storage stability of the ink, particularly, storage stability at a lower temperature.

The present invention has been completed on the basis of such findings, and it is an object of the present invention to provide an ink capable of satisfying the above-described characteristics (1) to (5) at a higher level, more specifically, for example, an ink permitting the stable formation of high-quality images on a wide variety of recording media, and having excellent ejection stability, ejection durability and storage stability.

Another object of the present invention is to provide an image recording process which permits the stable recording of high-quality images on a wide variety of recording media.

A further object of the present invention is to provide an image recording apparatus which permits the stable recording of high-quality images on a wide variety of recording media, and an ink cartridge, ink set and recording unit which can be used in such an apparatus.

A still further object of the present invention is to provide an ink capable of satisfying the above-described characteristics (1) to (5) at a higher level, more specifically, for example, an ink which permits the stable provision of high-quality images on a wide variety of recording media, has excellent ejection stability, ejection durability and storage stability, and is unlikely to cause clogging at an orifice after stopping recording for a while, even under various use environments, or even in the case where orifices are made minuter.

A yet still further Object of the present invention is to provide an image recording process by which high-quality images can be stably recorded on a wide variety of recording media, and high-quality images can be stably formed even under various use environments, or such an effect can be stably exhibited even in the case where orifices of a recording head are made minuter for the purpose of providing higher-quality images.

A yet still further object of the present invention is to provide an image recording apparatus by which high-quality images can be stably recorded on a wide variety of recording media, and high-quality images can be stably formed even under various use environments, or such an effect can be stably exhibited even in the case where orifices of a recording head are made minuter for the purpose of providing higher-quality images, and an ink cartridge, ink set and recording unit which can be used in such an apparatus.

The above objects can be achieved by the present invention described below.

According to the present invention, there is thus provided an ink comprising a water-soluble coloring material and bis(hydroxyethyl)sulfone in an aqueous medium and having a pH of from 9.5 to 12.

According to the present invention, there is also provided an image recording process, comprising the step of applying an ink comprising a water-soluble coloring material and bis(hydroxyethyl)sulfone in an aqueous medium and having a pH of from 9.5 to 12 to the image forming region of a recording medium.

According to the present invention, there is further provided an image recording apparatus, comprising a recording unit which has an ink container portion charged therein with an ink comprising a water-soluble coloring material and bis(hydroxyethyl) sulfone in an aqueous medium and having a pH of from 9.5 to 12, a means for applying the ink to a recording medium, and a means for feeding the ink to the first mentioned means, and a means for actuating the means for applying the ink to the recording medium in the recording unit in response to recording signals.

According to the present invention, there is still further provided an ink set, comprising in combination an ink comprising a first water-soluble coloring material and bis (hydroxyethyl)sulfone and having a pH of from 9.5 to 12, and another ink comprising a second water-soluble coloring material, wherein each of the first and second water-soluble coloring materials is a coloring material of a color selected from the group consisting of yellow, magenta, cyan, black, red, blue and green.

According to the present invention, there is yet still further provided an ink cartridge, comprising an ink container portion charged therein with an ink comprising a water-soluble coloring material and bis(hydroxyethyl) sulfone in an aqueous medium and having a pH of from 9.5 to 12.

According to the present invention, there is yet still further provided a recording unit, comprising an ink container portion charged therein with an ink comprising a water-soluble coloring material and bis(hydroxyethyl) sulfone in an aqueous medium and having a pH of from 9.5 to 12, a means for applying the ink to a recording medium, and a means for feeding the ink to the first mentioned means.

According to the present invention, there is yet still further provided an image recording process, comprising the step of applying an ink comprising a water-soluble coloring material, bis(hydroxyethyl) sulfone and urea in an aqueous medium and having a pH of from 9.5 to 12 to the image forming region of a recording medium by means of an image recording apparatus comprising a recording unit, which has an ink container portion charged therein with the ink, a recording head equipped with a means for ejecting the ink to a recording medium from an orifice of the size that 0.1 to 40 picoliters of the ink can be ejected by one ejection operation and a means for feeding the ink to the recording head, and a means for actuating the recording unit in response to recording signals.

According to the present invention, there is yet still further provided an image recording apparatus, comprising a recording unit, which has an ink container portion charged therein with an ink comprising a water-soluble coloring material, bis(hydroxyethyl)sulfone and urea in an aqueous medium and having a pH of from 9.5 to 12, a recording head equipped with a means for ejecting the ink to a recording medium from an orifice of the size that 0.1 to 40 picoliters of the ink can be ejected by one ejection operation and a means for feeding the ink to the recording head, and a means for actuating the recording unit in response to recording signals.

According to the present invention, there is yet still further provided a recording unit, comprising an ink container portion charged therein with an ink comprising a water-soluble coloring material, bis(hydroxyethyl)sulfone and urea in an aqueous medium and having a pH of from 9.5 to 12, a recording head equipped with a means for ejecting the ink to a recording medium from an orifice of the size that 0.1 to 40 picoliters of the ink can be ejected by one ejection operation and a means for feeding the ink to the recording head.

Incidentally, Japanese Patent Application Laid-Open No. 10-768 discloses an ink comprising a disperse dye, a compound for dispersing the disperse dye, and an aqueous liquid medium, wherein BHES is added to the ink, and the pH of the ink is adjusted to 7 to 9. However, this publication neither discloses the technical subjects related to the present invention nor describes any suggestion as to these subjects.

The action of the present invention will hereinafter be described. As described above, the present inventors have carried out investigations on ink comprising a water-soluble coloring material and BHES. As a result, it has been newly found that when the pH of such an ink is adjusted to 9.5 to 12, the occurrence of kogation on a heater can be prevented extremely effectively, and the storage stability of the ink is also improved, thus leading to completion of the present invention. Aggregation of the coloring material of this ink is scarcely observed even after the long-term storage thereof, the performance of the ink is stable, and excellent colored images can be stably provided on a wide variety of recording media. For some particular coloring materials, the storage stability of an ink containing such a coloring material may be improved in an alkaline region, since the solubility of the coloring material is enhanced. However, the effects found by this investigation have been clearly beyond the dependency on coloring materials. The reason why the above effects are brought about by such a composition is not clear. However, inferring from the structure of BHES, it is considered that interaction between the coloring material and BHES is greatly enhanced in the ink the pH of which has been adjusted to 9.5 to 12, and so the mutual association of the water-soluble coloring material dissolved in the aqueous medium is effectively prevented.

DESCRIPTION OF THE PREFERRED EMBODIMENTS

Figure 1:
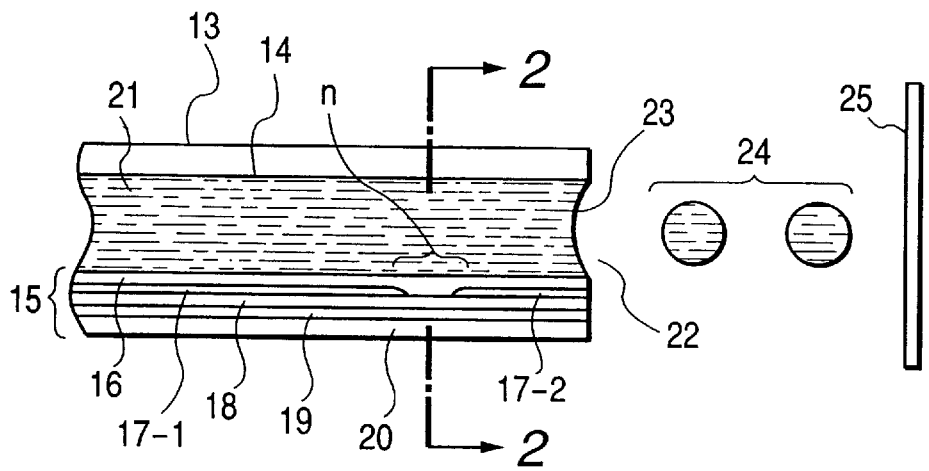
FIG. 1 is a longitudinal cross-sectional view of a head of an ink-jet recording apparatus according to an embodiment.

The present invention will hereinafter be described in detail by the preferred embodiments of the invention.

Definition of pH

The ink according to a first embodiment of the present invention comprises a water-soluble coloring material and BHES in an aqueous medium and has a pH of 9.5 to 12, particularly, 9.5 to 11.

BHES and its Amount Added

BHES has a structure represented by the following structural formula (I), and a commercially-available product synthesized by the conventionally known process may be used.

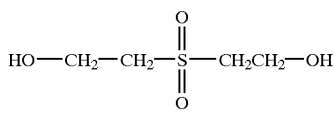

(I)

It is preferred that the content of BHES in the ink be 0.1 to 30% by weight, particularly 0.1 to 10% by weight, more particularly 0.5 to 10% by weight, based on the total weight of the ink. In the ink according to this embodiment, the effect of preventing the occurrence of kogation on a heater, which is an effect of the addition of BHES, is more enhanced by adjusting the pH of the ink to 9.5 to 12, so that the kogation-preventing effect can be effectively exhibited even when the content of BHES in the ink is reduced. According to such an ink, the relative content of the coloring material in the ink ejected from an orifice is increased, and thus there is a favorable influence on the optical density of the image.

Coloring Material and Content Thereof

No particular limitation is imposed on the coloring material so far as it interacts with BHES. However, for example, the conventionally-known water-soluble dyes, for example, direct dyes, acid dyes and reactive dyes, may be used. It is preferred that the content of the dye in the ink be 0.1 to 15% by weight, particularly 1 to 10% by weight, based on the total weight of the ink.

Aqueous Medium

The aqueous medium serves to hold BHES and the water-soluble dye in a state dissolved therein so as to make up the ink therefrom. The aqueous medium preferably contain at least water as a component. At least one water-soluble organic solvent may be mixed with water for the purpose of enhancing the solubility of various components contained in the ink or controlling the characteristics of the ink.

Content of Water

It is preferred that a proportion of water accounted for in the ink be, for example, 20 to 95% by weight, particularly 40 to 95% by weight, more particularly 60 to 95% by weight, based on the total weight of the ink. The content of the water-soluble organic solvent is within a range of preferably from 1 to 30% by weight, more preferably from 3 to 20% by weight, based on the total weight of the ink. When the amount of the organic solvent falls within this range, the sticking property of the ink when applied to a recording medium can be satisfied.

When the amounts of the respective components making up the ink are controlled within the above respective ranges, and the pH of the ink is controlled within the above range, the occurrence of kogation derived from BHES on the heater can be prevented extremely effectively as described above, and so the ejection durability of the ink can be still more improved. In addition, the optical density of an image formed on a recording medium with such an ink is also good, and moreover the fixing ability of the resulting image to a wide variety of recording media when conducting recording on the recording media is also excellent. Furthermore, even when the ink is stored for a long period of time, no change in quality is observed in the ink. Accordingly, such an ink may be used extremely suitably in ink-jet recording, particularly, an ink-jet recording method using a system wherein thermal energy is used to eject an ink.

Specific Examples of Coloring Material

Examples of the water-soluble coloring material used in this embodiment include the following coloring materials.
(Black ink)
Examples of dyes used in a black ink include C.I. Direct Black 17, C.I. Direct Black 19, C.I. Direct Black 22, C.I. Direct Black 31, C.I. Direct Black 32, C.I. Direct Black 51, C.I. Direct Black 62, C.I. Direct Black 71, C.I. Direct Black 74, C.I. Direct Black 112, C.I. Direct Black 113, C.I. Direct Black 154, C.I. Direct Black 168, C.I. Acid Black 2, C.I. Acid Black 48, C.I. Acid Black 51, C.I. Acid Black 52, C.I. Acid Black 110, C.I. Acid Black 115, C.I. Acid Black 156, C.I. Reactive Black 1, C.I. Reactive Black 8, C.I. Reactive Black 12, C.I. Reactive Black 13, C.I. Food B3lack 1 and C.I. Food Black 2.
(Yellow ink)
Examples of dyes used in a yellow ink include C.I. Acid Yellow 11, C.I. Acid Yellow 17, C.I. Acid Yellow 23, C.I. Acid Yellow 25, C.I. Acid Yellow 29, C.I. Acid Yellow 42, C.I. Acid Yellow 49, C.I. Acid Yellow 61, C.I. Acid Yellow 71, C.I. Direct Yellow 12, C.I. Direct Yellow 24, C.I. Direct Yellow 26, C.I. Direct Yellow 44, C.I. Direct Yellow 86, C.I. Direct Yellow 87, C.I. Direct Yellow 98, C.I. Direct Yellow 100, C.I. Direct Yellow 130 and C.I. Direct Yellow 142.
(Magenta ink)
Examples of dyes used in a magenta ink include C.I. Acid Red 1, C.I. Acid Red 6, C.I. Acid Red 8, C.I. Acid Red 32, C.I. Acid Red 35, C.I. Acid Red 37, C.I. Acid Red 51, C.I. Acid Red 52, C.I. Acid Red 80, C.I. Acid Red 85, C.I. Acid Red 87, C.I. Acid Red 92, C.I. Acid Red 94, C.I. Acid Red 115, C.I. Acid Red 180, C.I. Acid Red 254, C.I. Acid Red 256, C.I. Acid Red 289, C.I. Acid Red 315, C.I. Acid Red 317, C.I. Direct Red 1, C.I. Direct Red 4, C.I. Direct Red 13, C.I. Direct Red 17, C.I. Direct Red 23, C.I. Direct Red 28, C.I. Direct Red 31, C.I. Direct Red 62, C.I. Direct Red 79, C.I. Direct Red 81, C.I. Direct Red 83, C.I. Direct Red 89, C.I. Direct Red 227, C.I. Direct Red 240, C.I. Direct Red 242 and C.I. Direct Red 243.
(Cyan ink)
Examples of dyes used in a cyan ink include C.I. Acid Blue 9, C.I. Acid Blue 22, C.I. Acid Blue 40, C.I. Acid Blue 59, C.I. Acid Blue 93, C.I. Acid Blue 102, C.I. Acid Blue 104, C.I. Acid Blue 113, C.I. Acid Blue 117, C.I. Acid Blue 120, C.I. Acid Blue 167, C.I. Acid Blue 229, C.I. Acid Blue 234, C.I. Acid Blue 254, C.I. Direct Blue 6, C.I. Direct Blue 22, C.I. Direct Blue 25, C.I. Direct Blue 71, C.I. Direct Blue 78, C.I. Direct Blue 86, C.I. Direct Blue 90, C.I. Direct Blue a 106 and C.I. Direct Blue 199.

As other examples of water-soluble dyes, dyes having at least one —COOM group (in which M is an alkali metal, ammonium or organic ammonium) in their molecules may also be suitably used. Examples thereof include dyes represented by the following general formulae:

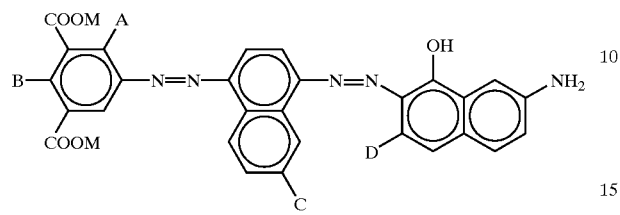
(II)

wherein A and B are independently a hydroxyl group or hydrogen, C is hydrogen or SO$_3$M, and D is SO$_3$M;

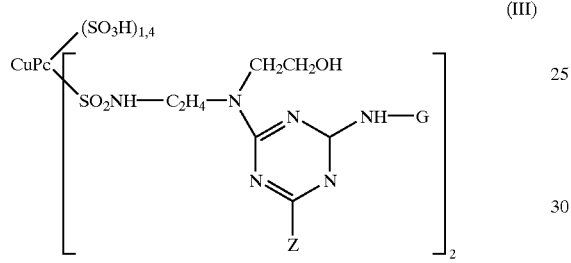
(III)

wherein G is any one of structures represented by the structural formulae

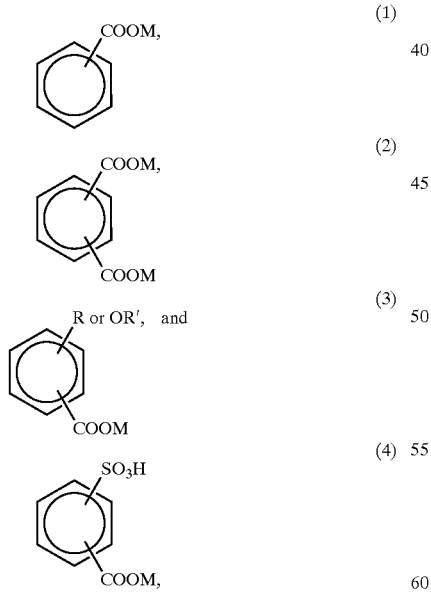

CuPc is a residue of copper phthalocyanine, and Z is NHCH$_2$CH$_2$OH or N(CH$_2$CH$_2$OH)$_2$, and in the structural formulae (1) to (4), R and R' are independently H or a lower alkyl group;

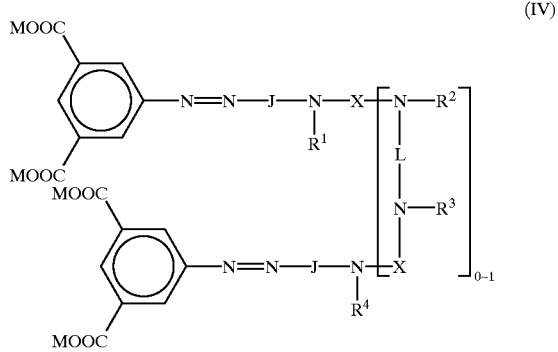
(IV)

wherein J is any one of structures represented by the structural formulae

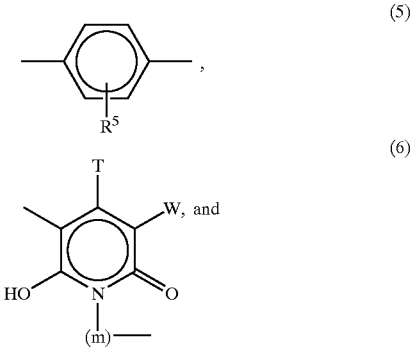

L is any one of structures represented by the structural formulae

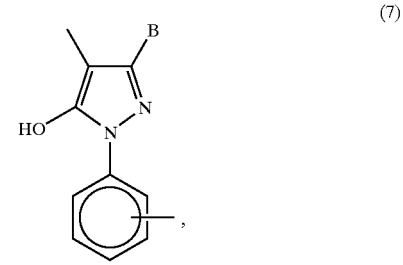

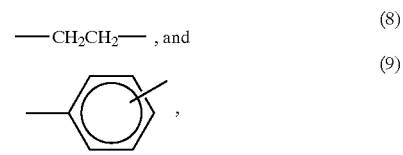

X is any one of structures represented by the structural formulae

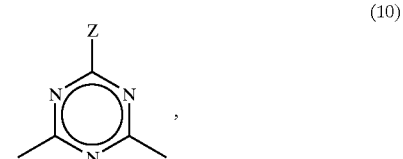

-continued

(11)
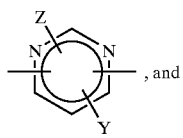, and

(12)
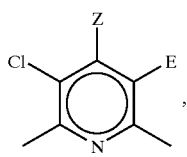

and $R^1$ to $R^4$ are independently H or a lower alkyl group, and in the structural formulae (5) to (12), B is H or COOH, W is H, CN, amide group, pyridinium group or COOH, m is a number of 2 to 8, Z is an alkoxy group, OH, alkylamino group or $NH_2$, Y is H, Cl or CN, E is Cl or CN, and $R^5$ is H or a lower alkyl group; and -continued

(17)
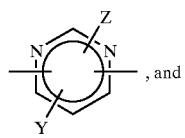, and

(18)
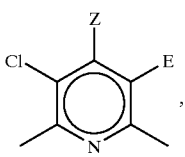

and $R^1$ and $R^2$ are independently H or a lower alkyl group, and in the structural formulae (13) to (18), Z is an alkoxy group, OH, alkylamino or $NH_2$, Y is H, Cl or CN, and E is Cl or CN.

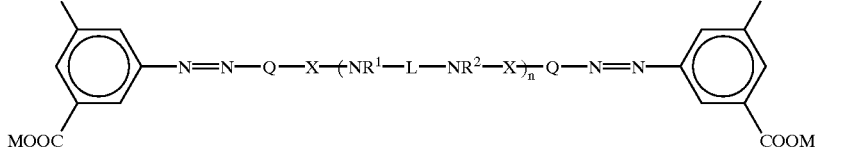
(V)

wherein Q is a structure represented by the structural formula

(13)
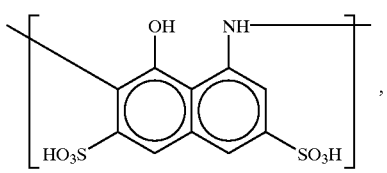,

L is any one of structures represented by the structural formulae

—CH$_2$CH$_2$—, and (14)

(15)
,

X is any one of structures represented by the structural formulae

(16)
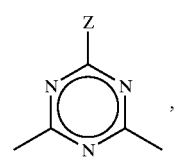,

Water-soluble Organic Solvent

Specific examples of the water-soluble organic solvent include amides such as dimethylformamide and dimethylacetamide; ketones such as acetone; ethers such as tetrahydrofuran and dioxane; polyalkylene glycols such as polyethylene glycol and polypropylene glycol; alkylene glycols the alkylene moiety of which has 2 to 6 carbon atoms, such as ethylene glycol, propylene glycol, butylene glycol, triethylene glycol, thiodiglycol, hexylene glycol and diethylene glycol; 1,2,6-hexanetriol; glycerol; lower alkyl ethers of polyhydric alcohols, such as ethylene glycol monomethyl (or monoethyl) ether, diethylene glycol monomethyl (or monoethyl) ether and triethylene glycol monomethyl (or monoethyl) ether; N-methyl-2-pyrrolidone; 1,3-dimethyl-2-imidazolidinone; triethanolamine; sulfolane; dimethyl sulfoxide; cyclic amide compounds such as 2-pyrrolidone and ε-caprolactam; imide compounds such as succinimide; and trimethylol-propane.

When the ink is made suitable for use in ink-jet recording, the ink is controlled so as to have, as its own physical properties as measured at 25° C., a surface tension of 30 to 68 dyn/cm and a viscosity of 15 cP or lower, particularly 10 cP or lower, more particularly 5 cP or lower by adjusting the materials and mixing proportions of the above respective components upon the preparation of the ink. By such adjustment, the ink-jet ejection properties of the ink become suitable for conducting recording of high-quality images. As specific ink compositions capable of achieving such properties, may be mentioned, for example, the compositions of inks described in Examples 1 to 6 which will be described subsequently.

Addition of Urea

As the ink according to a second embodiment of the present invention, may be mentioned an ink in which urea is further contained in addition to the components of the ink according to the first embodiment. According to the ink according to the second embodiment, improved reejecting ability compared with the conventional inks can be achieved in addition to the effects brought about by the ink according to the first embodiment. The term "reejection" as used herein means operation that an ink is ejected again from an orifice after suspending recording. From the investigations carried out up to this time, the present inventors have found that water-based inks containing a water-soluble coloring material include some inks which solidify at an orifice while suspending recording for a while to entirely or partly clog the orifice, resulting in an impossibility of reejecting ink or ejecting a predetermined amount of ink in the right direction, and that this tendency is often shown, particularly, in the case where orifices are made minuter for providing high-definition images or where use conditions are diversified with the spread of ink-jet recording apparatus, or in particular, an ink-jet recording apparatus is used in a low-temperature environment. However, the further addition of urea to the ink according to the first embodiment can also bring about the effect of stabilizing the reejecting ability even under the conditions described above in addition to the effects shown by the ink according to the first embodiment. The reason why the above effect is brought about by adopting the above embodiment is not clear. However, it is considered that since BHES is solid at ordinary temperatures and since it tends to be deposited in the form of wax if its proportion in the aqueous medium exceeds 80% by weight, this phenomenon microscopically arises also in a BHES-containing ink situated at an orifice with the evaporation of water in the ink. On the other hand, urea serves to strongly enhance the affinity of water for water-soluble dyes. Therefore, it is considered that when BHES is caused to coexist with urea, there is produced, in such an ink situated at an orifice, a synergistic effect between the effect of preventing the evaporation of water in the ink from the orifice by the deposition of BHES and the effect of preventing the rapid heightening of dye concentration in the ink in the vicinity of the orifice.

In this embodiment, it is preferred that the amount of urea be 0.1 to 20% by weight, particularly 0.1 to 15% by weight based on the total weight of the ink, while the total amount of urea and BHES be 0.2 to 30% by weight, particularly 0.6 to 25% by weight based on the total weight of the ink. Incidentally, to the inks according to the present invention, may be added various additives other than the above-described components, such as surfactants, pH adjusters, rust preventives, antiseptics, mildewproofing agents, antioxidants, evaporation accelerators, chelating agents and water-soluble polymers, as needed.

Apparatus

An ink-jet recording apparatus in which the above-described inks can be used, and an image recording process using it will hereinafter be described.

(Construction of head)

Figure 2:
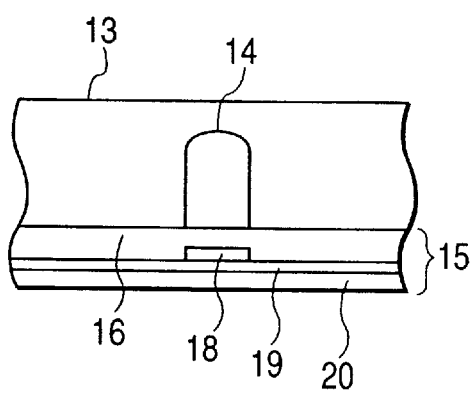
FIG. 2 is a transverse cross-sectional view taken along line 2—2 in FIG. 1.

FIG. 1 is a schematic cross-sectional view of a head according to an embodiment, which is a main component of an ink-jet recording apparatus of a system wherein thermal energy is used to eject an ink, taken along the longitudinal direction of an orifice part from which an ink is ejected, and FIG. 2 is a cross-sectional view taken along line 2—2 in FIG. 1. In FIGS. 1 and 2, the head 13 is formed by bonding a glass, ceramic or plastic plate or the like having a groove 14 through which an ink is passed, to a heating head 15, which is used for thermal recording (the drawings show a head to which, however, the invention is not limited). The heating head 15 is composed of a protective film 16 made of silicon oxide or the like, aluminum electrodes 17-1 and 17-2, a heating resistor layer 18 made of nichrome or the like, a heat accumulating layer 19, and a substrate 20 made of alumina or the like having a good heat radiating property. An ink 21 comes up to an ejection orifice (a minute opening) 22 and forms a meniscus 23 due to a predetermined pressure P. Now, upon application of electric signals to the electrodes 17-1 and 17-2, the heating head 15 rapidly generates heat at the region shown by "n" to form bubbles in the ink 21 which is in contact with this region. The meniscus 23 of the ink is projected by the pressure thus produced, and the ink 21 is ejected from the orifice 22 to a recording medium (for example, paper) 25 in the form of minute droplets 24 and applied to the image recording region of the recording medium 25, thereby recording an image.

Figure 3:
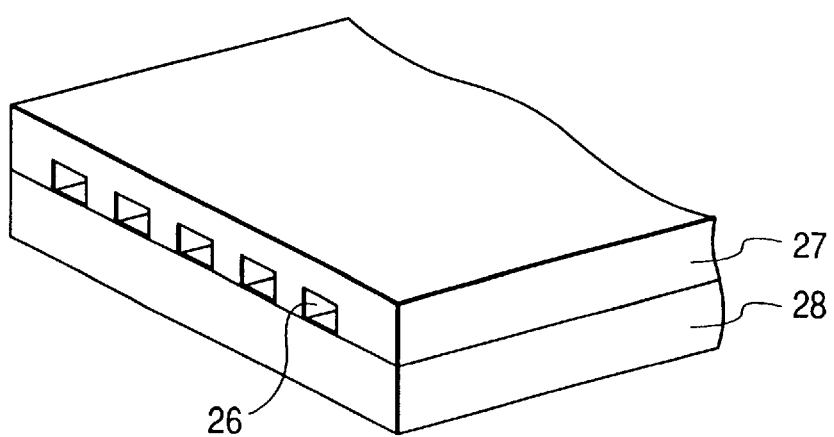
FIG. 3 schematically illustrates a multi-head.

FIG. 3 illustrates an appearance of a multi-head composed of an array of a number of heads as shown in FIG. 1. The multi-head is formed by closely bonding a glass plate 27 having a number of grooves 26 to a heating head 28 similar to the head as illustrated in FIG. 1.

In the construction of the heads described above, no particular limitation is imposed on the size of orifices, and it is only necessary to suitably preset the size according to the desired image quality. With the demand for the formation of high-quality images in recent years, however, there has been research to make the size of orifices minuter. More specifically, there has been research to make orifices so minute that an amount of an ink ejected from each orifice in one ejection operation amounts to 0.1 to 40 picoliters (pl), particularly 0.1 to 30 pl, more particularly 1 to 15 pl. In the orifices of such a size, a particularly preferred technical goal for the purpose of forming high-quality images is to stably reeject an ink after suspending recording for a while. The above-described inks according to the various embodiments of the present invention, particularly, the ink according to the second embodiment may be mentioned as an extremely effective technique capable of achieving this technical goal. Even when orifices are not made minute as described above, an ejection failure of ink may be caused in some cases due to clogging at an orifice as described above when an ink-jet recording apparatus is used in various environments with the spread of ink-jet recording apparatus, specifically, in an environment (for example, in a room where heating does not effectively act, or the outdoors in a cold district) that ambient temperature is 5° C. or lower by way of example. This respect may also be mentioned as an important technical goal to achieve from the viewpoint of the wider spread of the ink-jet recording apparatus. The above-described inks according to the embodiments, particularly, the ink according to the second embodiment may be mentioned as an extremely effective technique capable of achieving this technical goal.

(Ink-jet recording apparatus)

Figure 4:
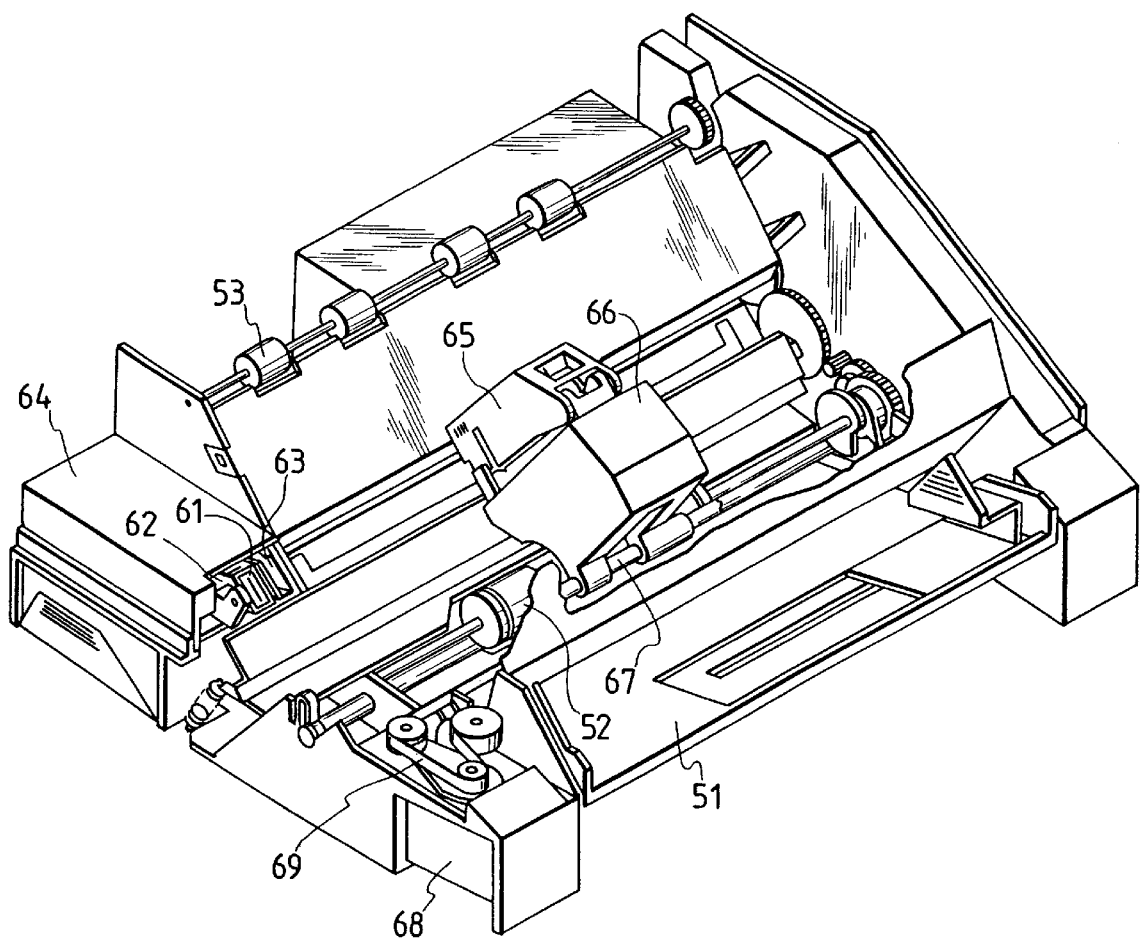
FIG. 4 is a schematic perspective view illustrating an ink-jet recording apparatus according to an embodiment.

FIG. 4 illustrates an example of an ink-jet recording apparatus in which such a head as described above has been incorporated. In FIG. 4, reference numeral 61 designates a blade serving as a wiping member, one end of which is a stationary end held by a blade-holding member to form a cantilever. The blade 61 is provided at a position adjacent to a region in which a recording head 65 operates, and in this embodiment, is held in such a form that it protrudes into the course through which the recording head 65 is moved. Reference numeral 62 indicates a cap which is provided at a home position adjacent to the blade 61, and is so constructed that it moves in a direction perpendicular to a direction in which the recording head 65 is moved, and comes into contact with the face of ejection openings to cap it. Reference numeral 63 denotes an absorbing member provided adjoiningly to the blade 61 and, similar to the blade 61, held in such a form that it protrudes into the course through which the recording head 65 is moved. The above-described blade 61, cap 62 and absorbing member 63 constitute an ejection-recovery portion 64, where the blade 61 and absorbing member 63 remove water, dust and/or the like from the face of the ink-ejecting openings. Reference numeral 65 designates the recording head having an ejection-energy-generating means and serving to eject the ink onto a recording medium set in an opposing relation to the ejection opening face provided with the ejection openings to conduct recording. Reference numeral 66 indicates a carriage on which the recording head 65 is mounted so that the recording head 65 can be moved. The carriage 66 is slidably interlocked with a guide rod 67 and is connected (not illustrated) at its part to a belt 69 driven by a motor 68. Thus, the carriage 66 can be moved along the guide rod 67 and hence, the recording head 65 can be moved from a recording region to a region adjacent thereto. Reference numerals 51 and 52 denote a paper feeding part from which the recording paper is inserted, and paper feed rollers driven by a motor (not illustrated), respectively. With such a construction, the recording paper is fed to the position opposite to the ejection opening face of the recording head 65, and discharged from a discharge section provided with discharge rollers 53 with the progress of recording.

In the above construction, the cap 62 in the head recovery portion 64 is receded from the path of motion of the recording head 65 when the recording head 65 is returned to its home position, for example, after completion of recording, and the blade 61 remains protruded into the path of motion. As a result, the ejection opening face of the recording head 65 is wiped. When the cap 62 comes into contact with the ejection opening face of the recording head 65 to cap it, the cap 62 is moved so as to protrude into the path of motion of the recording head 65.

When the recording head 65 is moved from its home position to the position at which recording is started, the cap 62 and the blade 61 are at the same positions as the positions for the wiping as described above. As a result, the ejection opening face of the recording head 65 is also wiped at the time of this movement. The above movement of the recording head 65 to its home position is made not only when the recording is completed or the recording head 65 is recovered for ejection, but also when the recording head 65 is moved between recording regions for the purpose of recording, during which it is moved to the home position adjacent to each recording region at given intervals, where the ejection opening face is wiped in accordance with this movement.

(Ink cartridge)

Figure 5:
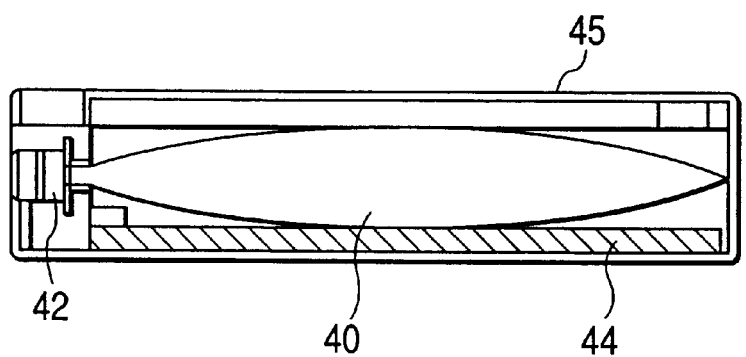
FIG. 5 is a longitudinal cross-sectional view of an ink cartridge according to an embodiment.

FIG. 5 illustrates an exemplary ink cartridge 45 in which an ink to be fed to a head through an ink-feeding member, for example, a tube is contained. Here, reference numeral 40 designates an ink container portion containing the ink to be fed, as exemplified by a bag for the ink. One end thereof is provided with a stopper 42 made of rubber. A needle (not illustrated) may be inserted into this stopper 42 so that the ink in the bag 40 for the ink can be fed to the head. Reference numeral 44 indicates an absorbing member for receiving a waste ink. It is preferred that the ink container portion be formed of a polyolefin, in particular, polyethylene, at its surface with which the ink comes into contact. The ink-jet recording apparatus used in the present invention are not limited to the apparatus as described above in which the head and the ink cartridge are separately provided. Therefore, a device in which these members are integrally formed as shown in FIG. 6 can also be preferably used.

(Recording unit)

Figure 6:
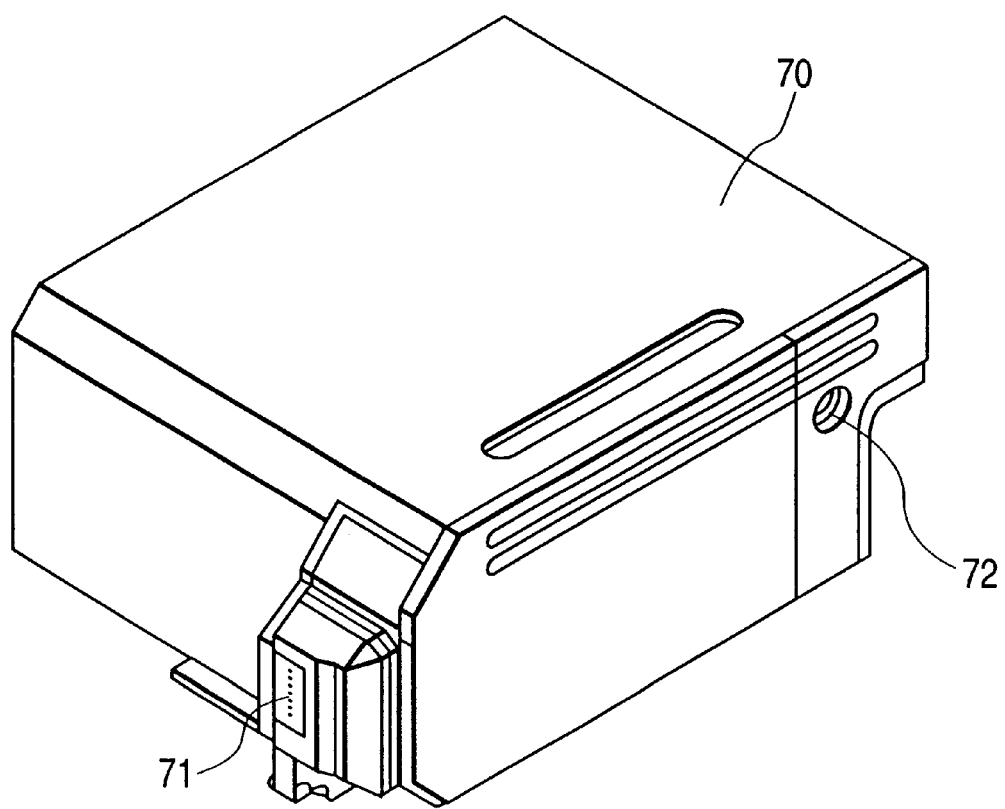
FIG. 6 is a schematic perspective view illustrating another exemplary construction of an ink-jet recording head.

In FIG. 6, reference numeral 70 designates a recording unit, in the interior of which an ink container portion containing an ink, for example, an ink-absorbing member, is contained. The recording unit 70 is so constructed that the ink in such an ink-absorbing member is ejected in the form of ink droplets through a head 71 having a plurality of orifices. In the present invention, polyurethane is preferably used as a material for the ink-absorbing member. Reference numeral 72 indicates an air passage for communicating the interior of the recording unit 70 with the atmosphere. This recording unit 70 can be used in place of the recording head 65 shown in FIG. 4, and is detachably installed on the carriage 66.

Ink Set

Figure 7:
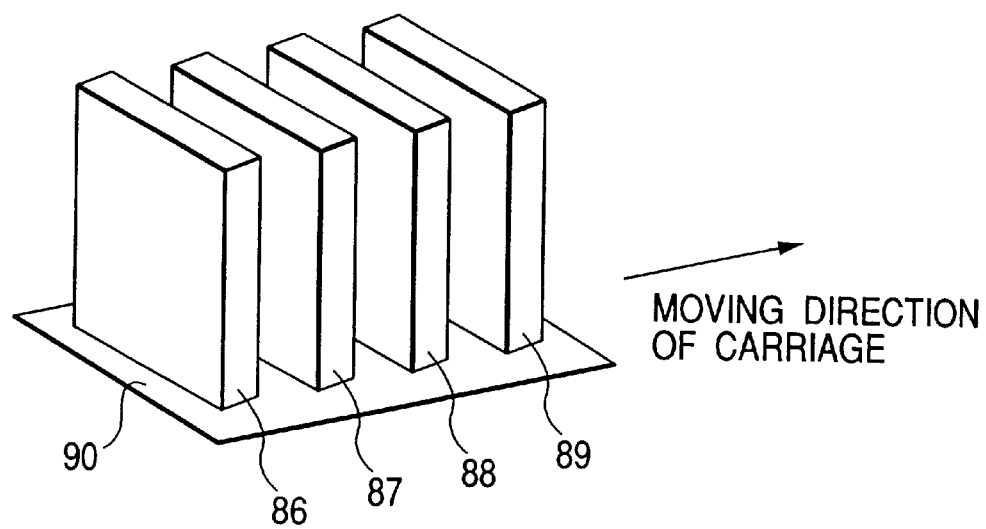
FIG. 7 schematically illustrates the construction wherein four recording heads are arranged on a carriage.
Figure 8:
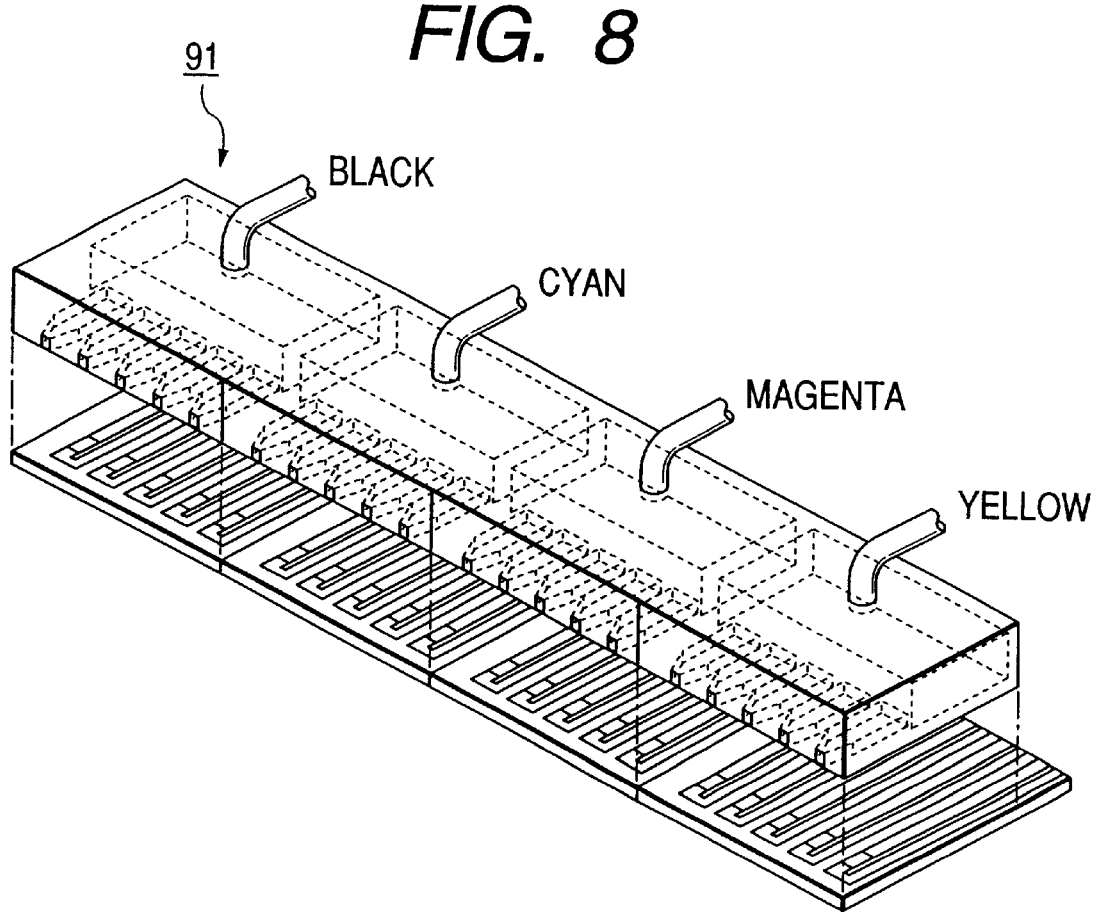
FIG. 8 schematically illustrates a recording head in which four ink cartridges are installed.

The above-described inks according to the various embodiments can be provided as, for example, yellow, magenta, cyan, red, green, blue or black inks by selecting a coloring material. These inks may be used singly in recording of images. Two or more inks of different colors may be combined to provide an ink set suitable for use in the formation of color images. Alternatively, two or more inks of the same color respectively containing coloring materials of different kinds, or two or more inks of the same color, which are different in dye concentration, may be combined to provide an ink set suitable for use in the formation of high-tone images. When these ink sets are used to form images, for example, a recording apparatus in which 4 recording heads, each of which has been illustrated in FIG. 3, are arranged on a carriage 90, may be used. An example thereof is illustrated in FIG. 7. Reference numerals 86, 87, 88 and 89 indicate recording heads for ejecting, for example, yellow, magenta, cyan and black inks, respectively. The recording heads are arranged in the above-described recording apparatus and serve to eject the respective inks in response to recording signals. FIG. 7 shows the case where the four recording heads have been used, however, the present invention is not limited thereto. For example, an embodiment, wherein ink cartridges for the above four colors are used to conduct recording of color images through separate ink flow paths in one recording head 91 as shown in FIG. 8, is also included.

The examples where the inks according to the present invention are used in the apparatus wherein thermal energy according to recording signals is applied to an ink, and the ink is ejected by the thermal energy, and the image recording processes using such an apparatus have been described above. However, the inks according to the present invention may also be used in ink-jet recording apparatus of a system wherein an ink is ejected by mechanical energy, and image recording processes using such an apparatus, whereby the same excellent effects can be achieved.

The present invention will hereinafter be described more specifically by the following Examples and Comparative Examples. Incidentally, all designations of "part" or "parts" and "%" as will be used in the following examples mean part or parts by weight and % by weight unless expressly noted.

EXAMPLES 1 TO 4

Their corresponding components shown in Table 1 were mixed and thoroughly stirred into solutions, and the resultant solutions were separately filtered under pressure through a Fluoropore Filter (trade name, product of Sumitomo Electric Industries, Ltd.) having a pore size of 0.45 μm, thereby preparing inks according to Examples 1 to 4.

COMPARATIVE EXAMPLES 1 TO 4

Their corresponding components shown in Table 2 were used to prepare inks according to Comparative Examples 1 to 4 following the same procedure as in Examples 1 to 4.

Dye 1 used in Example 3 and Comparative Example 3 has a structure represented by the structural formula

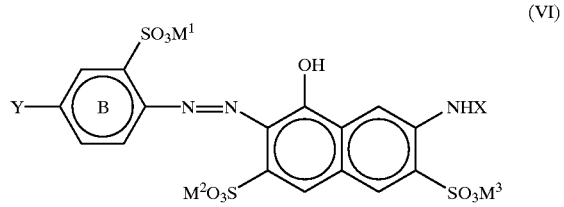

(VI)

wherein Y is hydrogen, or a methyl, methoxy, acetylamino or nitro group, or may form a benzene ring together with the carbon atom situated at the 3-position of the benzene ring B, X is an acetyl, benzoyl, p-toluenesulfonyl or 4-chloro-6-hydroxy-1,3,5-triazin-2-yl group, $M^1$, $M^2$ and $M^3$ are independently a base selected from alkali metals, ammonium and amines.

TABLE 1

|  | Ex. 1 | Ex. 2 | Ex. 3 | Ex. 4 |
| --- | --- | --- | --- | --- |
| BHES | 10 | 5 | 3 | 8 |
| Glycerol | 0 | 5 | 11 | 6 |
| Diethylene glycol | 3 | 0 | 6 | 0 |
| Thiodiglycol | 3 | 5 | 0 | 7 |
| C.I. Food Black 2 | 4 | 3.5 | 0 | 0 |
| C.I. Direct Blue 199 | 0 | 0 | 0 | 4 |
| Dye 1 | 0 | 0 | 4 | 0 |
| Acetylenol EH (trade name, product of Kawaken Fine Chemicals Co., Ltd.) | 0.1 | 0 | 0.8 | 0 |
| Ethanol | 4 | 5 | 0 | 3 |
| Ammonium sulfate | 0.05 | 0 | 0.1 | 0 |
| Water | 75.85 | 76.5 | 75.1 | 72 |
| Sodium hydroxide | To pH 10.5 | To pH 9.5 | To pH 11 | To pH 10 |

TABLE 2

|  | Comp. Ex. 1 | Comp. Ex. 2 | Comp. Ex. 3 | Comp. Ex. 4 |
| --- | --- | --- | --- | --- |
| BHES | 10 | 0 | 0 | 0 |
| Glycerol | 0 | 5 | 14 | 6 |
| Diethylene glycol | 3 | 0 | 6 | 8 |
| Thiodiglycol | 3 | 5 | 0 | 7 |
| C.I. Food Black 2 | 4 | 3.5 | 0 | 0 |
| C.I. Direct Blue 199 | 0 | 0 | 0 | 4 |
| Dye 1 | 0 | 0 | 4 | 0 |
| Acetylenol EH (trade name, product of Kawaken Fine Chemicals Co., Ltd.) | 0.1 | 0 | 0.8 | 0 |
| Ethanol | 4 | 5 | 0 | 3 |
| Ammonium sulfate | 0.05 | 0 | 0.1 | 0 |
| Water | 75.85 | 81.5 | 75.1 | 72 |
| Sodium hydroxide | — | To pH 9.5 | — | — |

TABLE 2-continued

|  | Comp. Ex. 1 | Comp. Ex. 2 | Comp. Ex. 3 | Comp. Ex. 4 |
| --- | --- | --- | --- | --- |
|  | (about pH 7) | 9.5 | (about pH 7) | (about pH 10) |

The inks according to Examples 1 to 4 and Comparative Examples 1 to 4 obtained above were used to conduct a printing test using, as an ink-jet recording apparatus, an On-Demand type ink-jet printer (ink volume ejected from an orifice by one ejection operation: 25 pl; printing density: 720 dpi) making good use of a heating element, thereby evaluating the inks as to (1) optical density of image, (2) fixing ability, (3) ejection durability and (4) storage stability in accordance with the following respective standards. The evaluation results thus obtained are shown in Tables 3 and 4.

Evaluation Methods and Standards (1) Optical Density of Image:

After a solid print image was printed on PPC paper (product of Canon Inc.) by the printer and air-dried for 24 hours in a room, its optical density was measured by a Macbeth RD915 (trade name, manufactured by Macbeth Company), and evaluation was made in accordance with the following standard:

AA: Optical density was higher than 1.35;

A: Optical density was from 1.30 to 1.35;

B: Optical density was from 1.20 to 1.29; and

C: Optical density was lower than 1.20.

(2) Fixing Ability:

A solid print was printed on PPC paper (product of Canon Inc.) and glossy film (CA-101, trade name; product of Canon Inc.) by the printer. After 10 seconds, the solid print area was rubbed with filter paper (No. 5C, trade name; product of Toyo Filter Paper Co., Ltd.). Evaluation was then made in accordance with the following standard:

A: No staining occurred on the print in 10 seconds;

B: Slight staining occurred on the print in 10 seconds; and

C: Marked staining occurred on the print in 10 seconds.

(3) Ejection Durability:

After each of the ink samples was ejected repeatedly $1 \times 10^8$ times by means of the printer, printing was conducted on PPC paper (product of Canon Inc.). The evaluation was then made as to the ejection durability in terms of the state of the surface of a heater in accordance with the following standard:

A: No deposit was observed on the heater;

B: Some deposit was observed on the heater; and

C: A large amount of deposit was observed on the heater.

(4) Storage Stability:

An ink sample was placed in a container and left to stand for 1 month in an environment controlled at 5° C. The evaluation was then made in accordance with the following standard:

A: No aggregate was observed in the ink;
B: Fine aggregate was slightly observed in the ink; and
C: Fine aggregate was observed in the ink.

TABLE 3

|  |  | Ex. 1 | Ex. 2 | Ex. 3 | Ex. 4 |
|---|---|---|---|---|---|
| 1. Optical density |  | AA | AA | AA | AA |
| 2. Fixing ability | PPC paper | A | A | A | A |
|  | CA-101 | A | A | A | A |
| 3. Ejection durability |  | A | A | A | A |
| 4. Storage stability |  | A | A | A | A |

TABLE 4

|  |  | Comp. Ex. 1 | Comp. Ex. 2 | Comp. Ex. 3 | Comp. Ex. 4 |
|---|---|---|---|---|---|
| 1. Optical density |  | AA | A | A | B |
| 2. Fixing ability | PPC paper | A | A | A | B |
|  | CA-101 | A | A | B | C |
| 3. Ejection durability |  | B | C | C | B |
| 4. storage stability |  | B | C | B | B |

EXAMPLES 5 AND 6

Inks of their corresponding compositions shown in Table 5 were prepared and evaluated in the same manner as in Examples 1 to 4. In addition, the inks were separately used to conduct recording on commercially-available paper for copying by means of the same printer as that used for the evaluation in Examples 1 to 4 and Comparative Examples 1 to 4, thereby evaluating them as to (5) clogging tendency upon reprinting after suspending printing, and (6) responsiveness to frequency. The evaluation was made under the following respective conditions:

(5) Clogging Tendency Upon Reprinting After Suspending Printing:

After the printer was charged with each ink sample, and English characters and numerals were continuously printed for 1 minute in an environment of 20° C. in room temperature and 25±5% in humidity, the printing was suspended for 30 seconds and then resumed. The clogging tendency was evaluated by whether defective printed areas such as blurred characters and chipped characters were present or not, and ranked in accordance with the following standard. At this time, the head temperature was 35±5° C.

A: No blur was observed even from the first character;
B: A part of the first character was blurred or chipped; and
C: The first character was not printed at all.

(6) Responsiveness to Frequency:

Each resulting print sample was observed by naked eyes with respect to its printing conditions, namely, conditions of blurred characters and blank areas, and defective ink-droplet impact such as splash and slippage to evaluate the ink sample in the responsiveness to frequency in accordance with the following standard:

AA: The follow-up characteristics of the ink to the frequency was good, and none of blurred characters, blank areas and defective ink-droplet impact was observed upon both solid printing and character printing;

A: The follow-up characteristics of the ink to the frequency was substantially good, and none of blurred characters, blank areas and defective ink-droplet impact was observed upon character printing, but blur was slightly observed upon solid printing;

B: Neither blur nor blank areas was observed, but defective ink-droplet impact was partly observed upon character printing, and blur and blank areas were observed at portions of about one-third of the whole solid printed area upon solid printing; and C: Blur and blank areas were observed to a great extent upon solid printing, and blur and defective ink-droplet impact were also observed to a large extent upon character printing.

The evaluation results thus obtained are shown in Tables 5 and 6.

TABLE 5

|  | Example 5 | Example 6 |
|---|---|---|
| BHES | 7 | 4 |
| Glycerol | 4 | 5 |
| Diethylene glycol | 3 | 0 |
| Urea | 3 | 4 |
| Thiodiglycol | 0 | 4 |
| C.I. Food Black 2 | 3.5 | 0 |
| Dye 1 | 0 | 3.5 |
| Ethanol | 4 | 5 |
| Ammonium sulfate | 0 | 0 |
| Water | 75.5 | 74.5 |
| Sodium hydroxide | To pH 9.5 | To pH 10 |

TABLE 6

|  |  | Ex. 5 | Ex. 6 |
|---|---|---|---|
| 1. Optical density |  | AA | AA |
| 2. Fixing ability | PPC paper | A | A |
|  | CA-101 | A | A |
| 3. Ejection durability |  | A | A |
| 4. Storage stability |  | A | A |
| 5. Clogging tendency after suspending printing |  | A | A |
| 6. Frequency responsiveness |  | A | A |

According to the respective embodiments of the present invention, as described above, there can be provided inks, ink sets, ink cartridges, recording units, image recording methods and image recording apparatus which can satisfy the following characteristics or properties (1) to (5) at an extremely high level:

(1) providing clear or bright images having a high optical density;

(2) providing high-quality images free of any undefined or irregular feathering;

(3) having high fixing ability to recording media;

(4) being excellent in ejection stability; and (5) having good storage stability.

More specifically, there can be provided inks, ink sets, ink cartridges and recording units which can stably provide high-quality images on a wide variety of recording media (for example, coated paper prepared for ink-jet, and non-coated paper (so-called plain paper) such as paper for copying, paper for reporting, notepaper, letter paper, bond paper and continuous business forms, which are commonly used in offices and homes), scarcely undergo changes in ejection performance, and have excellent storage stability.

In addition, they permit stable recording of high-quality images on the various recording media.

There can also be provided inks, ink sets, ink cartridges and recording units that can stably provide high-quality images on a wide variety of recording media, scarcely undergo changes in ejection performance, have excellent storage stability, and are unlikely to cause clogging at an orifice after suspending recording for a while even under various use environments or even in the case where orifices are made minuter.

Further, according to the image recording processes and apparatus of the present invention, high-quality images can be stably recorded on a wide variety of recording media, and high-quality images can be stably formed even under various use environments, and clogging at an orifice can be effectively prevented even in the case where orifices are made minuter for the purpose of providing higher-quality images.

What is claimed is:

1. An ink comprising a water-soluble coloring material and bis(hydroxyethyl) sulfone in an aqueous medium and having a pH of from 9.5 to 12.

2. The ink according to claim 1, wherein bis-(hydroxyethyl) sulfone is contained in an amount of 0.1 to 10% by weight based on the total weight of the ink.

3. The ink according to claim 1, which further comprises urea.

4. The ink according to claim 3, wherein urea is contained in an amount of 0.1 to 20% by weight based on the total weight of the ink.

5. The ink according to claim 3 or 4, wherein bis(hydroxyethyl) sulfone and urea are contained in an amount of 0.2 to 30% by weight in total based on the total weight of the ink.

6. The ink according to claim 1, wherein the ink is for ink-jet recording.

7. An image recording process, comprising the step of applying an ink comprising a water-soluble coloring material and bis(hydroxyethyl) sulfone in an aqueous medium and having a pH of from 9.5 to 12 to an image forming region of a recording medium.

8. The image recording process according to claim 7, wherein the ink further comprises urea.

9. The image recording process according to claim 8, wherein urea is contained in an amount of 0.1 to 20% by weight based on the total weight of the ink.

10. The image recording process according to claim 8 or 9, wherein bis(hydroxyethyl) sulfone and urea are contained in an amount of 0.2 to 30% by weight in total based on the total weight of the ink.

11. An image recording apparatus, comprising a recording unit which has an ink container portion charged therein with an ink comprising a water-soluble coloring material and bis(hydroxyethyl) sulfone in an aqueous medium and having a pH of from 9.5 to 12, a means for applying the ink to a recording medium, and a means for feeding the ink to the first mentioned means, and a means for actuating the means for applying the ink to the recording medium in the recording unit in response to recording signals.

12. The image recording apparatus according to claim 11, wherein the ink further comprises urea.

13. The image recording apparatus according to claim 12, wherein urea is contained in an amount of 0.1 to 20% by weight based on the total weight of the ink.

14. The image recording apparatus according to claim 12 or 13, wherein bis(hydroxyethyl) sulfone and urea are contained in an amount of 0.2 to 30% by weight in total based on the total weight of the ink.

15. An ink set, comprising in combination an ink comprising a first water-soluble coloring material and bis(hydroxyethyl) sulfone and having a pH of from 9.5 to 13, and another ink comprising a second water-soluble coloring material, wherein each of the first and second water-soluble coloring materials is a coloring material of a color selected from the group consisting of yellow, magenta, cyan, black, red, blue and green.

16. The ink set according to claim 15, wherein the ink containing the first water-soluble coloring material further comprises urea.

17. The ink set according to claim 16, wherein urea is contained in an amount of 0.1 to 20% by weight based on the total weight of the ink.

18. The ink set according to claim 16 or 17, wherein bis(hydroxyethyl) sulfone and urea are contained in an amount of 0.2 to 30% by weight in total based on the total weight of the ink.

19. An ink cartridge, comprising an ink container portion charged therein with an ink comprising a water-soluble coloring material and bis(hydroxyethyl) sulfone in an aqueous medium and having a pH of from 9.5 to 12.

20. The ink cartridge according to claim 19, wherein the ink further comprises urea.

21. The ink cartridge according to claim 20, wherein urea is contained in an amount of 0.1 to 20% by weight based on the total weight of the ink.

22. The ink cartridge according to claim 20 or 21, wherein bis(hydroxyethyl) sulfone and urea are contained in an amount of 0.2 to 30% by weight in total based on the total weight of the ink.

23. A recording unit, comprising an ink container portion charged therein with an ink comprising a water-soluble coloring material and bis(hydroxyethyl) sulfone in an aqueous medium and having a pH of from 9.5 to 12, a means for applying the ink to a recording medium, and a means for feeding the ink to the first mentioned means.

24. The recording unit according to claim 23, wherein the ink further comprises urea.

25. The recording unit according to claim 24, wherein urea is contained in an amount of 0.1 to 20% by weight based on the total weight of the ink.

26. The recording unit according to claim 24 or 25, wherein bis(hydroxyethyl) sulfone and urea are contained in an amount of 0.2 to 30% by weight in total based on the total weight of the ink.

27. An image recording process, comprising the step of applying an ink comprising a water-soluble coloring material, bis(hydroxyethyl) sulfone and urea in an aqueous medium and having a pH of from 9.5 to 12 to the image forming region of a recording medium by means of an image recording apparatus comprising a recording unit, which has an ink container portion charged therein with the ink, a recording head equipped with a means for ejecting the ink to a recording medium from an orifice of the size that 0.1 to 40 picoliters of the ink can be ejected by one ejection operation and a means for feeding the ink to the recording head, and a means for actuating the recording unit in response to recording signals.

28. An image recording apparatus, comprising a recording unit, which has an ink container portion charged therein with an ink comprising a water-soluble coloring material, bis(hydroxyethyl) sulfone and urea in an aqueous medium and having a pH of from 9.5 to 12, a recording head equipped with a means for ejecting the ink to a recording medium from an orifice of the size that 0.1 to 40 picoliters of the ink can be ejected by one ejection operation and a means for feeding the ink to the recording head, and a means for actuating the recording unit in response to recording signals.

29. A recording unit, comprising an ink container portion charged therein with an ink comprising a water-soluble coloring material, bis(hydroxyethyl) sulfone and urea in an aqueous medium and having a pH of from 9.5 to 12, a recording head equipped with a means for ejecting the ink to a recording medium from an orifice of the size that 0.1 to 40 picoliters of the ink can be ejected by one ejection operation and a means for feeding the ink to the recording head.

30. An ink-jet recording apparatus comprising:
an ink container containing an ink for ink-jet recording; and
an ink-jet head for ejecting the ink,
wherein the ink comprises a water-soluble coloring material and bis(hydroxyethyl) sulfone in an aqueous medium, and has a pH of from 9.5 to 12.

31. A process for ink-jet recording comprising the steps of:
(i) providing an ink for ink-jet recording; and
(ii) applying the ink by an ink-jet process,
wherein the ink comprises a water-soluble coloring material, bis(hydroxyethyl) sulfone and an aqueous medium, and
wherein the ink has a pH of from 9.5 to 12.

* * * * *

UNITED STATES PATENT AND TRADEMARK OFFICE
CERTIFICATE OF CORRECTION

PATENT NO. : 6,412,936 B1
DATED : July 2, 2002
INVENTOR(S) : Kumiko Mafune et al.

It is certified that error appears in the above-identified patent and that said Letters Patent is hereby corrected as shown below:

<u>Title page,</u>
Item [56], References Cited, FOREIGN PATENT DOCUMENTS, "10095107" should read -- 10-095107 --.

<u>Column 1,</u>
Line 13, "using" should read -- using it. --.

<u>Column 6,</u>
Line 33, "B3lack 1" should read -- Black 1 --.

<u>Column 19,</u>
Line 65, "13," should read -- 12, --.

Signed and Sealed this

Seventeenth Day of December, 2002

JAMES E. ROGAN
*Director of the United States Patent and Trademark Office*